US004001649B2

United States Statutory Invention Registration [19]

[11] Reg. Number: H1649

Barrish et al.

[45] Published: May 6, 1997

[54] HIV PROTEASE INHIBITOR COMBINATIONS

[76] Inventors: Joel C. Barrish, 46 Heather Valley Rd., Holland, Pa. 18966; Richard J. Colonno, 5288 Lower Mountain Rd., Buckingham, Pa. 18938; Pin-Fang M. Lin, 169 Northford Rd., Branford, Conn. 06405

[21] Appl. No.: 436,868

[22] Filed: May 17, 1995

Related U.S. Application Data

[63] Continuation-in-part of Ser. No. 270,614, Jul. 5, 1994, which is a continuation-in-part of Ser. No. 79,978, Jul. 31, 1987, Pat. No. 4,987,228.

[51] Int. Cl.[6] ..... A01N 43/00; A61K 31/395

[52] U.S. Cl. ..... 514/210

[58] Field of Search ..... 514/237.5, 238.8, 514/239.5

[56] References Cited

U.S. PATENT DOCUMENTS 5,484,926 1/1996 Dressman et al. ..... 546/114

FOREIGN PATENT DOCUMENTS 580402 1/1994 European Pat. Off. .

OTHER PUBLICATIONS

HIV–1 Protease Inhibitors: Their Development, Mechanism of Action and Clinical Potential, D. Pillay et al, *Rev. Med. Virol.*, 5: 23–33, 1995.

D. pillay et al., "HIV–1 Protease Inhibitors: . . . Clin. Potential", Rev. Med. Virol., vol. 5, pp. 23–33.

*Primary Examiner*—Charles T. Jordan
*Assistant Examiner*—Meena Chelliah
*Attorney, Agent, or Firm*—David M. Morse

[57] ABSTRACT

Combinations of certain HIV-1 protease inhibitors are provided which effectively inhibit the HIV-1 protease enzyme while eliminating or substantially reducing the viral cross-resistance seen with use of individual HIV-1 protease inhibitors. Such combinations are useful in the treatment of diseases associated with the AIDS virus.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HIV PROTEASE INHIBITOR COMBINATIONS

CROSS REFERENCE TO RELATED APPLICATIONS

This is a continuation-in-part of our pending U.S. patent application Ser. No. 08/270,614 filed Jul. 5, 1994, which is a continuation-in-part of our U.S. patent application Ser. No. 07/79,978 filed Jul. 31, 1987, now U.S. Pat. No. 4,987,228, issued on Jan. 22, 1991, which parent application is hereby incorporated by reference in its entirety.

BACKGROUND OF THE INVENTION

The present invention relates to combinations of antiviral agents. More particularly, it relates to combinations of HIV-1 protease inhibitors which exhibit lack of cross-resistance and are thus desirable in the clinical treatment of HIV infection.

Human Immunodeficiency Virus (HIV-1) is the causative agent of Acquired Immunodeficiency Syndrome (AIDS) in man. There are currently only three drugs approved for the treatment of HIV infection in the United States, AZT (zidovudine; Retrovir®), DDI (didanosine, Videx®) and DDC (zalcitabine, Hivid®). All three are members of the nucleoside analog class which inhibit the activity of the HIV-1 reverse transcriptase enzyme. These nucleoside analogs have shown efficacy in the clinical setting. However, none of them appear to halt disease progression, and treatment, particularly with AZT, results in viral variants that have significantly reduced drug sensitivity.

The HIV-1 reverse transcriptase has proven to be a very accommodating enzyme that is capable of harboring several amino acid substitutions that render it resistant to individual nucleoside analogs or a combination of nucleoside and/or non-nucleoside analogs.

HIV-1 also encodes an aspartyl protease enzyme that plays an essential role in reproduction of the virus late in infection and represents an attractive target for drug intervention. Recently, several inhibitors of this protease have been reported in the literature. Since these protease inhibitors, unlike reverse transcriptase inhibitors, have the ability to inhibit the production of infectious virus particles in chronically-infected cells, they are promising candidates for anti-HIV therapy.

Our parent U.S. application Ser. No. 07/79,978 filed Jun. 25, 1993 describes novel aminediol HIV-1 protease inhibitors of the following formula I

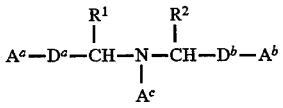

(I)

where $A^a$, $A^b$ and $A^c$ are independently:

(1) hydrogen;

(2) alkyl, especially lower alkyl;

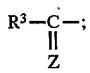

(3)

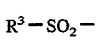

(4)

-continued

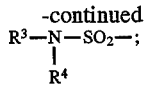

(5)

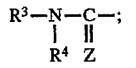

(6)

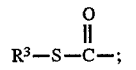

(7)

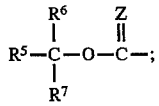

(8)

or

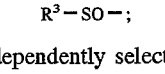

(9)

$D^a$ and $D^b$ are independently selected from groups of the formula:

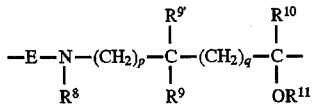

where $D^a$ and $D^b$ are bonded to the groups $A^a$ and $A^b$, respectively, through the moiety —E—N($R^8$)—, where E is a single bond or a peptide chain containing 1 to 4 amino acids, the N-terminus of which is bonded to $A^a$ when E is part of $D^a$ or to $A^b$ when E is part of $D^b$;

$R^1$ and $R^2$ are independently:

(1) hydrogen;

(2) alkyl, especially lower alkyl;

(3) alkenyl, especially lower alkenyl;

(4) aryl;

(5) heterocyclo; or (6) carbocyclo, such as cycloalkyl;

$R^3$ and $R^4$ are independently:

(a) hydrogen;

alkyl, especially lower alkyl;

(c) aryl;

(d) heterocyclo;

(e) carbocyclo, such as cycloalkyl;

(f) when $R^3$ and $R^4$ are bonded to a common nitrogen atom, $R^3$ and $R^4$ may be joined, together with that nitrogen atom, to form a heterocyclic ring system, such as a 5 to 7 membered heterocyclic ring; or (g) when E is a single bond and $R^3$ is part of $A^a$ or $A^b$, $R^3$ may, together with $R^8$, form an alkylene group, for example, having one to five carbons, such as wherein $R^3$ and $R^8$, together with the atoms to which they are bonded, form the cyclic moiety:

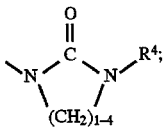

$R^5$, $R^6$ and $R^7$ are independently:

(a) hydrogen;

(b) alkyl, especially lower alkyl;

(c) aryl;

(d) carbocyclo, such as cycloalkyl;

(e) fluorenyl;

(f) heterocyclo;

(g) $R^5$, $R^6$ and $R^7$ may, independently, be joined, together with the carbon atom to which they are bonded, to form a mono-, bi- or tricyclic carbocyclic ring system, especially wherein each ring contains 3 to 7 carbon atoms, or a mono-, bi- or tricyclic heterocyclic ring system;

(h) alkynyl;

(i) alkenyl; or (g) when E is a single bond and $R^5$, $R^6$ and $R^7$ are part of $A^a$ or $A^b$, one of $R^5$, $R^6$, or $R^7$ may, together with $R^8$, form an alkylene group, for example, having one to three carbons, such as wherein $R^5$ and $R^6$ are methyl and $R^7$ and $R^8$, together with the atoms to which they are bonded, form the cyclic moiety:

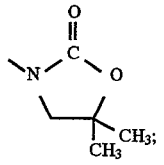

$R^8$ is:

(a) hydrogen;

(b) alkyl, especially unsubstituted lower alkyl or aryl-lower alkyl;

(c) $R^8$ and $R^9$ may be joined, together with the atoms to which they are bonded, to form a heterocyclic ring system, for example, a 5 to 7 membered monocyclic heterocyclic ring;

(d) $R^8$ may be joined together with $R^5$, $R^6$ or $R^7$ as described above;

(e) $R^8$ may be joined together with $R^3$ as described above; or (f) $R^8$ and $R^{11}$ may be joined, together with the atoms to which they are bonded, to form a heterocyclic ring system, such as where $R^8$ and $R^{11}$ together are an alkylene group;

$R^9$ and $R^{9'}$ are independently:

(a) hydrogen;

(b) alkyl, especially lower alkyl;

(c) alkenyl, especially lower alkenyl;

(d) alkynyl;

(e) aryl (f) heterocyclo;

(g) carbocyclo, such as cycloalkyl;

(h) $R^9$ may be joined together with $R^8$ as described above; or (i) $R^9$ and $R^{9'}$ may be joined, together with the carbon atom to which they are bonded, to form a carbocyclic group, such as 5- or 6-membered carbocyclic ring;

$R^{10}$ is:

(a) hydrogen;

alkyl, such as unsubstituted lower alkyl or hydroxy-lower alkyl, cycloalkyl-lower alkyl, aryl-lower alkyl or heterocyclo-lower alkyl;

(c) alkenyl, especially lower alkenyl;

(d) alkynyl;

(e) carbocyclo, such as cycloalkyl;

(f) aryl; or (g) $R^{10}$ and $R^{11}$ taken together may form a bond to give a keto (C=O) group;

$R^{11}$ is:

(a) hydrogen;

(b) a hydroxyl protecting group, such as alkyl;

(c) $R^{11}$ may be joined together with $R^8$ as described above; or (d) $R^{11}$ may, together with $R^{10}$, form a bond to give a keto group as described above;

Z is oxygen or sulfur; and p and q are, independently, integers from 0 to 4; and salts, preferably pharmaceutically acceptable salts, thereof. Among the compounds disclosed is [1S-[1R*,2S*(2S*,3R*)]]-[3-[[3-[[(1,1-dimethylethoxy)carbonyl]amino]-2-hydroxy-4-(4-[2-(4-morpholinyl)-2-oxo-ethoxy]phenyl]butyl]amino]-2-hydroxy-1-(phenylmethyl)propyl]carbamic acid, 1,1-dimethylethyl ester, the structure of which is as follows:

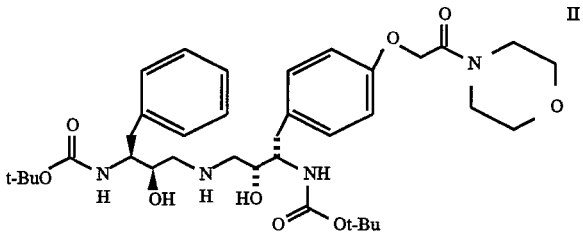

II

This compound will also be referred to below as BMS-186318.

Preferred embodiments of BMS-186318 include the pharmaceutically acceptable salts formed with inorganic and/or organic acids, e.g. succinic acid, acetic acid, hydrochloric acid, fumaric acid, citric acid, malic acid, methanesulfonic acid, benzenesulfonic acid, phosphoric acid, maleic acid and tartaric acid. The succinate salt of BMS-186318 is a particularly preferred embodiment.

EP 432695 A2 discloses the Hoffmann-LaRoche HIV-1 protease inhibitor of the formula

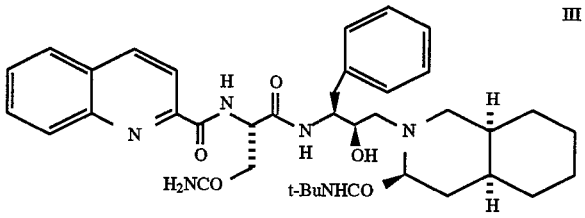

III which is known as saquinavir or Ro 31-8959. This compound has the chemical name N-tert.butyl-decahydro-2(2(R)-hydroxy-4-phenyl-3(S)-[[N-(2-quinolylcarbonyl)-L-asparaginyl)amino)butyl]-(4aS,8aS)-isoquinoline-3(S)-carboxamide.

PCT Published Application WO 92/08688 discloses the Monsanto-Searle HIV-1 protease inhibitor designated SC-52151 having the formula

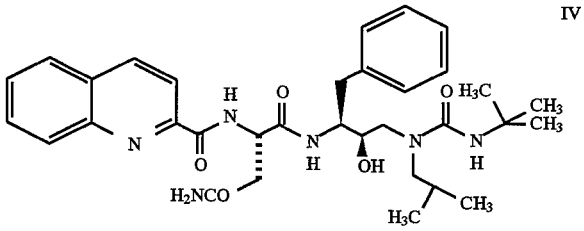

IV and the chemical name [1S-[1R*(R*), 2S*]]-$N^1$[3-[[[(1,1-dimethylethyl)amino]-carbonyl](2-methylpropyl)amino]-2-hydroxy-1-(phenylmethyl)propyl]-2-[(2-quinolinylcarbonyl)amino]-butanediamide.

EP 402646 A1 discloses the Abbott HIV-1 protease inhibitor designated A-77003 having the formula

V

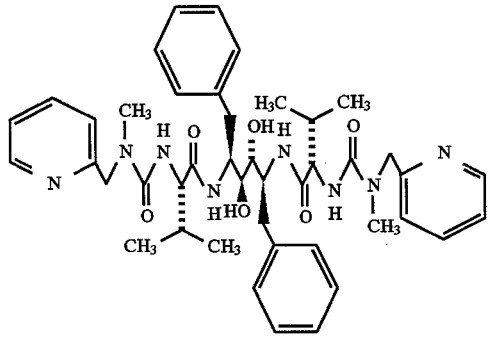

and the chemical name (2S,3R,4S,5S)-2,5-di-(N-((N-methyl-N-((2-pyridinyl)methyl)amino)carbonyl)-valinyl-amino)-3,4-dihydroxy-1,6-diphenylhexane.

The Abbott HIV-1 protease inhibitor designated ABT-538 having the formula

VI

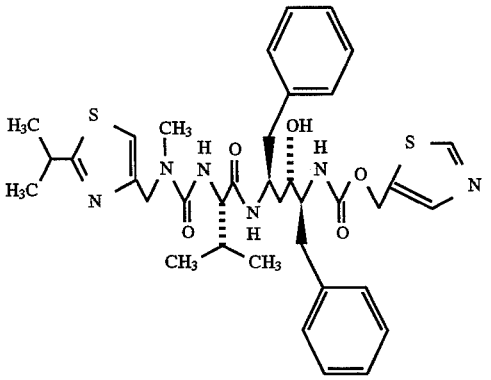

and the chemical name, [1S-(1R,2R,4R)]-N-[2-hydroxy-5-phenyl-1-(phenylmethyl)-1-[[(5-thiazolylmethoxy)carbonyl]amino]pentyl]-$N^2$-[[N-methyl[[2-(1-methylethyl)-4-thiazolyl]methyl]amino]carbonyl]L-valinamide, is generically disclosed in EP 486948 A2 and specifically disclosed in an abstract for the 207th American Chemical Society meeting (Mar. 13–17, 1994) held in San Diego, Calif.

EP 486948 A2 discloses the Abbott HIV-1 protease inhibitor designated A-80987 having the formula

VII

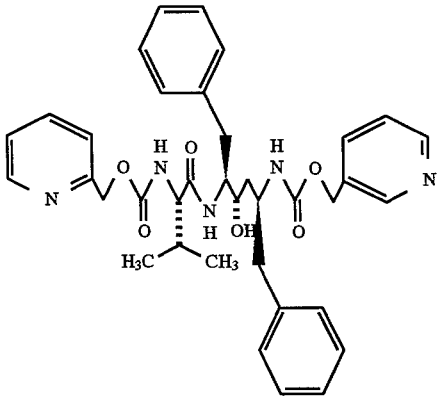

and the chemical name (2S,3S,5S)-2-(N-(N-((2-pyridinyl)methoxycarbonyl)-valinyl)amino)-5-(N-((3-pyridinyl)methoxycarbonyl)amino)-1,6-diphenyl-3-hydroxyhexane.

EP 541168 A1 discloses the Merck HIV-1 protease inhibitor designated L-735,524 having the formula

VIII

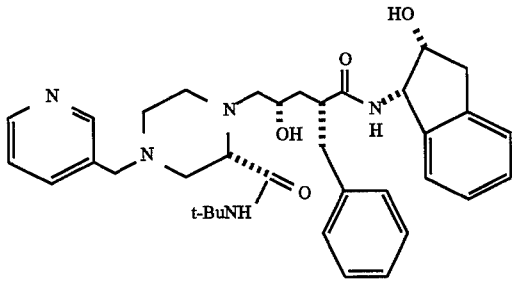

and the chemical name N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide.

The Agouron HIV-1 protease inhibitor designated AG-1343 having the formula

IX

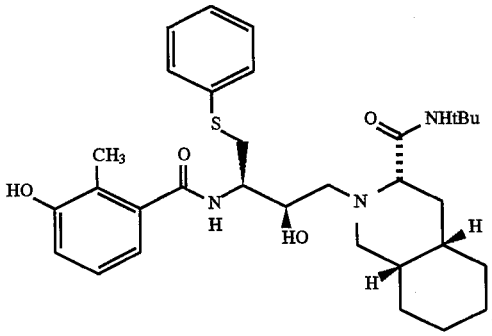

and the chemical name [3S-[2(2S*,3S*)3a,4ab,8ab]]-N-(1,1-dimethylethyl)decahydro-2-[2-hydroxy-3-[(3-hydroxy-2-methylbenzoyl)amino]-4-(phenylthio)butyl]-3-isoquinolinecarboxamide was disclosed, for example, by V. Kalish of Agouron at the 1st Winter Bioorganic/Medicinal Chemistry Symposium held at Steamboat Springs, Colorado on January 29–Feb. 2, 1995 (see also, *Rev. Med. Virol.* 5: 23–33, 1995).

AG-1343 may be prepared by reacting the amine of the formula

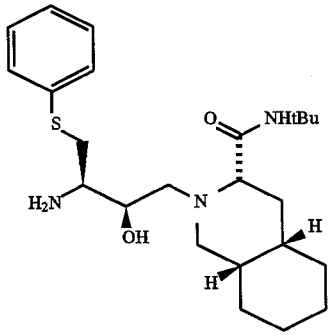

(prepared as described in Jungheim, et al., European Published Application 604,185A1) with the acid

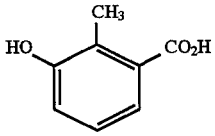

(prepared as described in U.S. Pat. No. 5,110,979; Houbion, et al. in *Org. Prep. Proced. Int.*, 1979, 11, 27; and Cresp, et al., in *J. Chem. Soc. Perkins Trans. I,* 1974, 2435) under standard peptide coupling conditions, e.g. 1-(3-dimethylaminopropyl)-3-ethylcarbodiimide(EDC)/hydroxybenzotriazole (HOBT).

The above-described Hoffmann-LaRoche, Monsanto-Searle, Agouron, Abbott and Merck HIV-1 protease inhibitors have all been reported to be under clinical development for HIV infection.

Various suggestions have been made in the literature to combine antiviral drugs, including HIV protease inhibitors, with other antiviral agents (see, for example, *Antimicrob. Agents Chemother.* 36(3), 509–520, 1992; *J. Acquired Immune Deficiency Syndromes,* 3 (Suppl. 2), S99–S103, 1990; and *J. Acquired Immune Deficiency Syndromes,* 6, 162–170, 1993). PCT Application WO 94/02149 discloses the so-called convergent combination approach to antiviral therapy whereby an antivirally effective amount of three or more different agents are employed, each of which is capable of inhibiting the activity of the same gene product or gene of a virus.

Suppressing chronic HIV infection requires long-term therapy. We have found that although the HIV virus appears to have more difficulty becoming resistant to protease inhibitors than to non-nucleoside reverse transcriptase inhibitors, resistance eventually does develop to HIV protease inhibitors. In-vitro drug sensitivity assays on the HIV-1 protease inhibitors currently in clinical trials have demonstrated unique resistance profiles, suggesting that combination of two or more protease inhibitors may be an effective approach to inhibiting HIV replication.

It is an object of the present invention to provide certain combinations of HIV-1 protease inhibitors which, when used either concurrently or sequentially, overcome the drug resistance seen with use of individual HIV-1 protease inhibitors or many combinations of HIV-1 protease inhibitors.

SUMMARY OF THE INVENTION

In one aspect this invention provides pharmaceutical compositions for prophylaxis or treatment of diseases caused by the HIV virus comprising an effective HIV-inhibiting amount of BMS-186318 having the formula

II

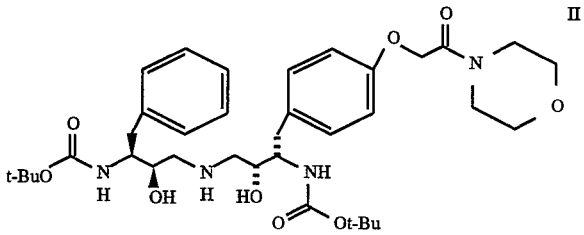

or a pharmaceutically acceptable derivative thereof, and an effective HIV-inhibiting amount of one or more HIV-1 protease inhibitors selected from the group consisting of (a) Ro 31-8959 having the formula

III

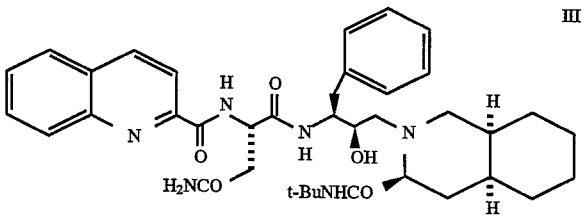

or a pharmaceutically acceptable derivative thereof, (b) SC-52151 having the formula

IV

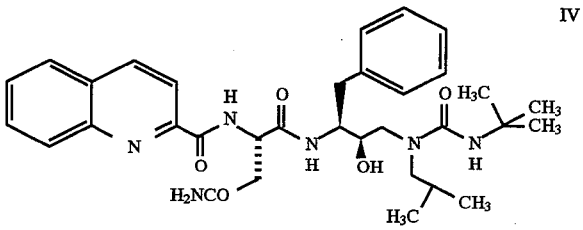

or a pharmaceutically acceptable derivative thereof, (c) A-77003 having the formula

V

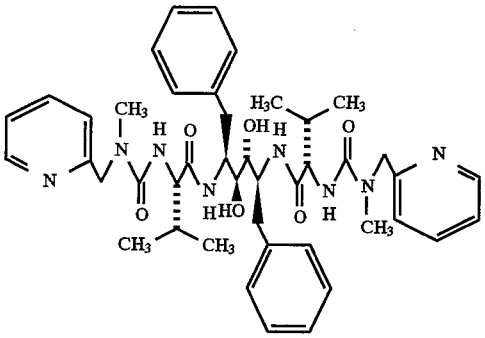

or a pharmaceutically acceptable derivative thereof, (d) A-80987 having the formula

VII

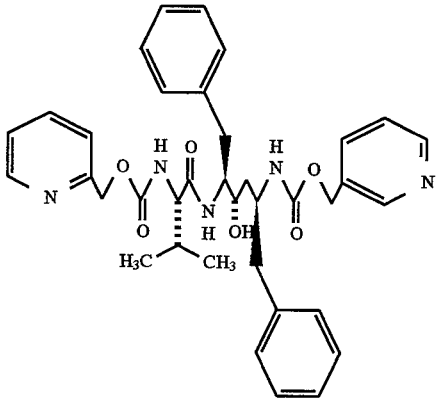

or a pharmaceutically acceptable derivative thereof, (e) L-735,524 having the formula

VIII

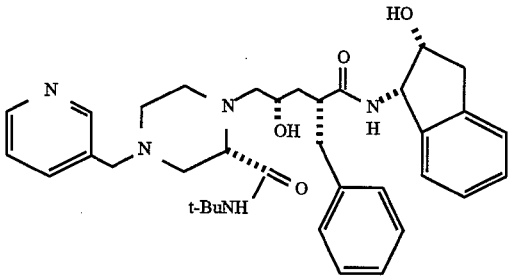

or a pharmaceutically acceptable derivative thereof, (f) ABT-538 having the formula

VI

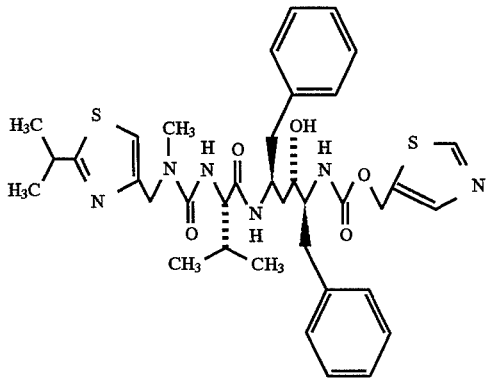

or a pharmaceutically acceptable derivative thereof, and (g) AG-1343 having the formula

IX

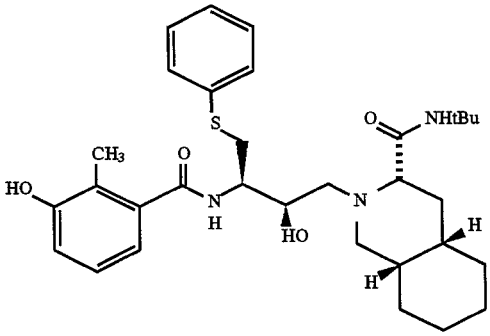

or a pharmaceutically acceptable derivative thereof, in combination with a pharmaceutically acceptable carrier or diluent.

In another aspect the present invention provides a method for the prophylaxis or treatment of diseases caused by the HIV virus in a human patient, which comprises administering to said patient, either sequentially or concurrently, an effective HIV-inhibiting amount of BMS-186318 having the formula

II

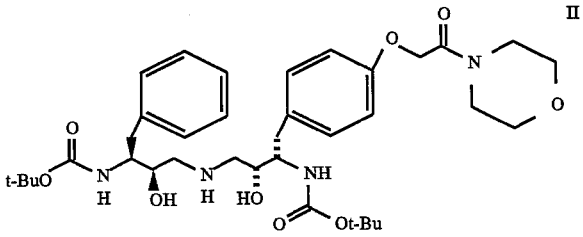

or a pharmaceutically acceptable derivative thereof, and an effective HIV-inhibiting amount of one or more HIV-1 protease inhibitors selected from (a) Ro 31-8959 having the formula

III

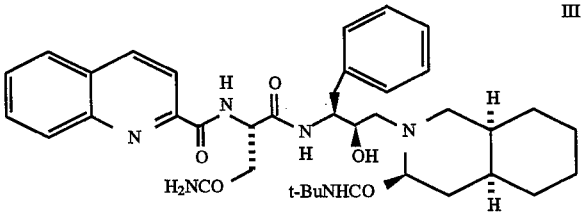

or a pharmaceutically acceptable derivative thereof, (b) SC-52151 having the formula,

IV

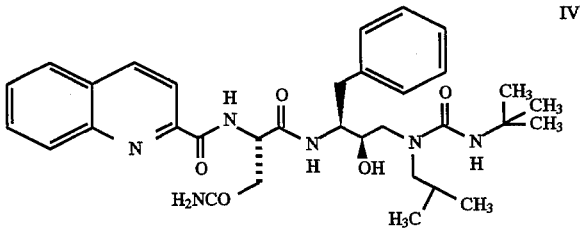

or a pharmaceutically acceptable derivative thereof, (c) A-77003 having the formula

V

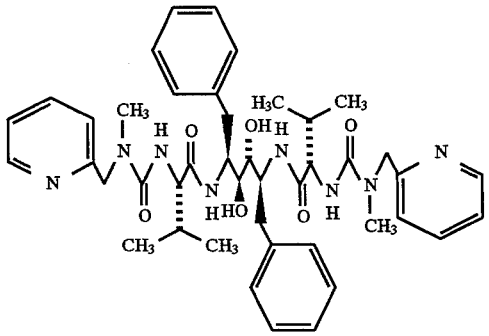

or a pharmaceutically acceptable derivative thereof, (d) A-80987 having the formula

VII

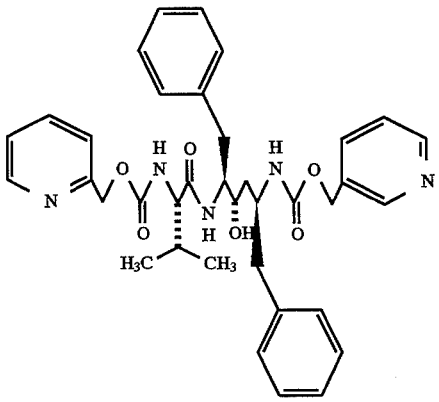

or a pharmaceutically acceptable derivative thereof, (e) ABT-538 having the formula

VI

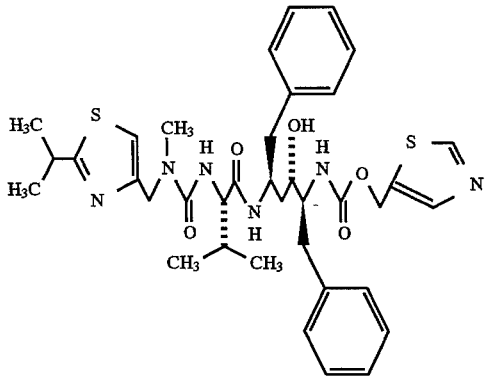

or a pharmaceutically acceptable derivative thereof, (f) L-735,524 having the formula

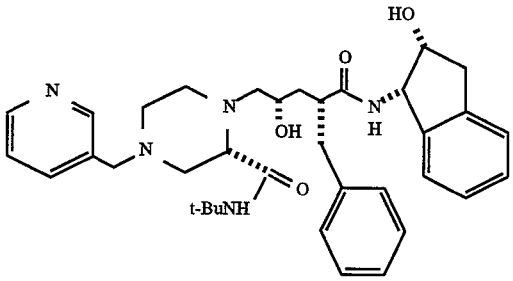

VIII or a pharmaceutically acceptable derivative thereof, and (g) AG-1343 having the formula

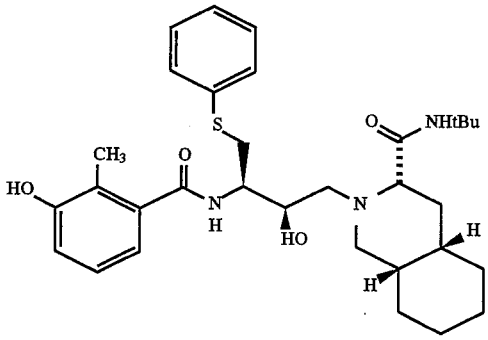

IX or a pharmaceutically acceptable derivative thereof.

In yet another aspect the present invention provides a method for reducing or eliminating resistance resulting from administration of an HIV-1 protease inhibitor selected from the group consisting of (a) Ro 31-8959, or a pharmaceutically acceptable derivative thereof, (b) SC-52151, or a pharmaceutically acceptable derivative thereof, (c) A-77003, or a pharmaceutically acceptable derivative thereof, (d) A-80987, or a pharmaceutically acceptable derivative thereof, (e) ABT-538, or a pharmaceutically acceptable derivative thereof, (f) L-735,524, or a pharmaceutically acceptable derivative thereof, and (g) AG-1343, or a pharmaceutically acceptable derivative thereof, or a combination of two or more of said inhibitors, which comprises administering either sequentially or concurrently, an effective HIV-inhibiting amount of BMS-186318, or a pharmaceutically acceptable derivative thereof.

DETAILED DESCRIPTION

Combination therapy has been proposed for treatment of antiviral diseases, including diseases associated with AIDS. In our parent application Ser. No. 07/79978 filed Jun. 25, 1993, we disclosed that the novel aminediol HIV-1 protease inhibitors of general formula I above could be used in combination with other antiviral agents, including other HIV protease inhibitors.

We have now found that BMS-186318, included within the scope of general formula I and specifically disclosed in Example 226 of our parent application, exhibits unexpected advantages when used in combination with certain other HIV-1 protease inhibitors. First, BMS 186,318 displays a synergistic antiviral effect in cell culture assays when used in combination with either Ro 31-8959 or SC-52151. Second, HIV-1 variants resistant to BMS 186,318 remain susceptible to inhibition by the other protease inhibitors. The surprising lack of cross-resistance seen with these combinations would be an important clinical advance in the treatment of diseases caused by HIV.

The term "a pharmaceutically acceptable derivative" as used herein is meant to include any pharmaceutically acceptable salt, prodrug or solvate of a compound of the present invention which, upon administration to the host, is capable of providing (directly or indirectly) the parent compound or an antivirally effective metabolite or residue thereof.

The term "pharmaceutically acceptable salt" as used herein denotes pharmaceutically acceptable acidic salts formed with inorganic and/or organic acids. Suitable pharmaceutically acceptable salts of the HIV-1 protease inhibitor compounds of the present invention are disclosed in EP 580402 A2, EP 432695 A2, WO 92/08688, EP 402646 A1, EP 486948 A2 and EP 541168 A1. Illustrative of such salts are acid addition salts formed from inorganic acids such as hydrochloric acid, hydrobromic, nitric acid, sulfuric acid and phosphoric acid and organic acids such as oxalic acid, acetic acid, maleic acid, lactic acid, glycolic acid, tartaric acid, succinic acid, methanesulfonic acid and citric acid.

The term "solvate" is meant to include both hydrates and solvates with organic solvents. Preferably, the solvates are hydrates.

Prodrugs of the HIV inhibitor compounds are also contemplated. The term "prodrug" as used herein denotes a compound which, upon administration to a patient, undergoes chemical conversion by metabolic or chemical processes to yield the parent compound, or a salt or solvate thereof. See H. Bundgaard, "Drugs of the Future", 16(5), 443–458 (1991) and H. Bundgaard(Ed.), "Design of Prodrugs", 1985 Elsevier (Amsterdam), both incorporated herein by reference.

A method for preparing BMS-186318 is disclosed below in Example 1. Methods for preparing the other HIV-1 protease inhibitors encompassed by the present invention are disclosed in the references disclosed above in connection with pharmaceutically acceptable salts and with AG-1343.

The BMS-186318 and the other HIV-1 protease inhibitor (s) may be administered either simultaneously (either separately or in combination) or sequentially. If administration is sequential, the delay in administering the active ingredients should not be such as to lose the benefit of the advantageous effect of the combination. Preferably, administration will be simultaneous.

Each compound is employed in the combination in an amount at which it exhibits HIV-inhibitory activity when used alone. Suitable dosage ranges are disclosed in the literature, e.g. see the patent references indicated above in connection with pharmaceutically acceptable salts.

For example, BMS-186318 may be administered in a total daily dosage of from about 1 to 150 mg/kg of body weight, preferably about 10 to 50 mg/kg of body weight. Ro 31-8959 may be administered in a daily dosage of from about 3 mg to about 3 grams, preferably about 10 mg to 1 gram. SC-52151 may be administered in a total daily dose of from about 0.001 to 10 mg/kg body weight, preferably 0.01 to 1 mg/kg. A-77003 may be administered in a daily dosage of from about 0.001 to 10 mg/kg, preferably 0.01 to 1 mg/kg of body weight. A-80987 may be administered in a total daily dose of from about 0.001 to 300 mg/kg body weight, preferably 0.1 to 10 mg/kg. L-735,524 may be administered in a total daily dosage of from about 0.02 to 10 grams. ABT-538 may be administered in a total daily dosage of from about 0.001 to 300 mg/kg of body weight. AG-1343 may be administered in a total daily dosage of from about 100 mg to 2000 mg.

It will be appreciated that the amount of a combination of the invention required for use in treatment will vary not only with the particular compounds selected but also with the route of administration, the nature of the condition being treated and the age and condition of the patient and, ultimately, will be at the discretion of the attendant physician. In general, however, a suitable daily dose will be in the range of from about 0.001 to about 300 mg/kg of body weight for each compound. A preferred dosage range would be in the range of between about 1 and about 50 mg/kg of body weight per day, administered as a single dose or in the form of individual divided doses, such as from 1–4 times per day.

The compositions of the present invention may be formulated, for example, by employing conventional solid or liquid vehicles or diluents, as well as pharmaceutical additives of a type appropriate to the mode of desired administration. The compounds may, for example, be administered orally, such as in the form of tablets, capsules, granules or powders; parenterally, such as by subcutaneous, intravenous, intramuscular or intrasternal injection or infusion techniques (e.g. as sterile injectable aqueous or non-aqueous solutions or suspension); topically, such as in the form of ointments, creams or lotions, or as a transdermal patch, or rectally such as in the form of suppositories; in dosage unit formulations containing non-toxic, pharmaceutically acceptable vehicles or diluents. The compounds may, for example, be administered liposomally.

When administered orally, the compositions may be prepared by techniques well-known in the art of pharmaceutical formulation. As a suspension they may, for example, contain microcrystalline cellulose for imparting bulk, alginic acid or sodium alginate as a suspending agent, methylcellulose as a viscosity enhancer, and sweeteners or flavoring agents known in the art. As immediate release tablets, the present compositions may contain microcrystalline cellulose, dicalcium phosphate, starch, magnesium stearate and/or lactose and/or other excipients, binders, extenders, disintegrants, diluents and lubricants known in the art.

When administered as injectable solutions or suspensions, the present compositions may be formulated according to techniques well-known in the pharmaceutical art, using suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides and fatty acids, including oleic acid.

When rectally administered in the form of suppositories, these compositions may be prepared by techniques well-known in the pharmaceutical art by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

For topical administration to the epidermis, the compositions may be formulated as lotions, ointments or creams, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Formulations suitable for topical administration to the mouth include lozenges, comprising active ingredient in a flavored base, usually sucrose and acacia or tragacanth; pastilles containing the active ingredient in an inert base such as gelatin and glycerin or sucrose and acacia; and mouthwashes comprising the active ingredient in a suitable liquid carrier.

The compositions of the present invention are useful in the inhibition of HIV protease, and thus in the prevention and/or treatment of infections caused by HIV viruses (HIV-1, HIV-2, and mutants thereof), including the treatment of consequent pathological conditions such as AIDS.

Use of the compositions of the present invention in inhibiting HIV protease includes, but is not limited to, treating a wide range of states of HIV infection such as treating or preventing AIDS or ARC (AIDS related complex), treating both symptomatic and asymptomatic HIV-infected patients, and treating actual or potential exposure to HIV. For example, the compositions of the present invention are useful in treating infection by HIV after suspected past exposure to HIV by, e.g. blood transfusion, accidental needle stick, or exposure to patient blood during surgery.

The following example illustrates the invention, but is not intended as a limitation thereof. The following abbreviations are employed in the example:

| | |
|---|---|
| Ph = | phenyl |
| t-Bu = | tertiary-butyl |
| Boc = | tert-butoxycarbonyl |
| Et = | ethyl |
| h = | hour(s) |
| THF = | tetrahydrofuran |
| DMF = | dimethylformamide |
| mol = | mole(s) |
| mmol = | millimole(s) |
| min = | minute(s) |
| RT = | room temperature |
| g = | gram(s) |
| ag = | aqueous |
| sat(sat'd) = | saturated |
| mg = | milligram(s) |
| TLC = | thin layer chromatography |
| EtOAc = | ethyl acetate |
| $Et_2O$ = | diethyl ether |
| eq = | equivalent(s) |
| i-PrOH = | isopropanol |
| MeOH = | methanol |
| n-$Bu_4NI$ = | tetra-n-butylammonium iodide |
| DME = | 1,2-dimethoxyethane |

EXAMPLE

Preparation of [IS-[IR*,2S*(2S*,3R*)]]-[3[[3-[[(1,1-dimethylethoxy) carbonyl]amino]-2-hydroxy-4-(4-[2-(4-morpholinyl)-2-oxo-ethoxy]phenyl]butyl] amino]-2-hydroxy-1-(phenylmethyl)propyl]carbamic acid 1,1-dimethylethyl ester (BMS-186318)

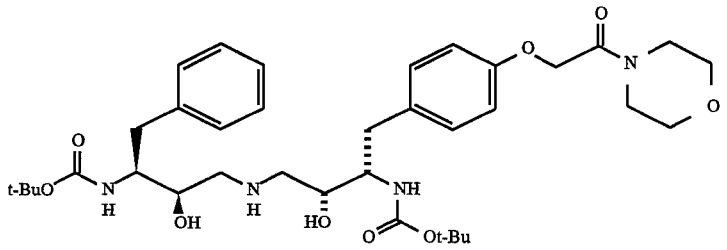

(i) Diazomethane-$Et_2O$ solution

To the mixture of 40% aqueous KOH (75 ml) and $Et_2O$ (255 ml) cooled at 0° C. was added 1-methyl-3-nitro-1-nitrosoguanidine (23.85 g, 162.2 mmol) portionwise. The mixture was swirled several times during each addition. After 10 min, the resulting yellow $Et_2O$ layer was decanted over KOH pellets at 0° C. and dried for 2.0 h at 0° C.

(ii) Compound 1

1

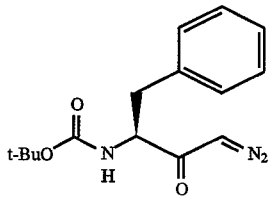

To the solution of N-Boc-L-phenylalanine (14.34 g, 54.05 mmol) in dry THF (80 ml) cooled at −20° C.(dry ice-$CCl_4$ bath) was added isobutyl chloroformate (7.01 ml, 54.05 mmol) over 5 min, followed by 4-methylmorpholine (5.94 ml, 54.05 mmol) and the mixture was stirred for 20 min. The white precipitate was removed by filtration under argon atmosphere and washed with ca. 70 ml of dry THF. The combined THF solution of mixed anhydride was cooled to −5° C. and poured into the above prepared diazomethane in $Et_2O$ solution at 0° C. The resulting yellow solution was kept at 0° C. for 2.0 h, then RT overnight. $N_2$ was then bubbled through the light-yellow solution for 30 min, and $Et_2O$ (400 ml) then added. The solution was washed with $H_2O$ (400 ml), saturated $NaHCO_3$ (300 ml) and brine (300 ml), and was dried over anhydrous $MgSO_4$. Concentration in vacuo afforded a yellow residue, which was triturated with hexane to give, after drying over $P_2O_5$ overnight under high vacuum, 14.72 g (94%) of α-diazoketone 1 as a pale yellow solid. This material was used immediately in the reaction of the next step without further purification.

(iii) Compound 2

2

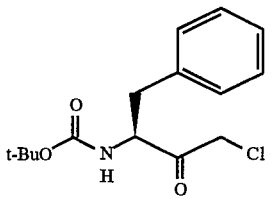

To the solution of the crude α-diazoketone 1 prepared above (14.72 g, 50.87 mmol) in dry $Et_2O$ (500 ml) cooled at 0° C. was added, dropwise, a solution of 4N HCl in dioxane (12.72 ml, 50.87 mmol) while maintaining the temperature below 5° C. The reaction mixture was then stirred at 0° C. for 1.0 h. TLC (hexane-EtOAc 4:1) showed trace amounts of the starting α-diazoketone remained. Additional 4N HCl in dioxane (636 μl, 0.05 eq., 2.54 mmol) was added and the mixture was stirred at 0° C. for one additional hour.

Concentration in vacuo gave a residue which was dissolved in hot $Et_2O$ (60 ml). Hexane (200 ml) was slowly added and the mixture allowed to stand for 2.0 h at 5° C. The solid was filtered and dried over $P_2O_5$ under high vacuum to afford 9.58 g (first crop) of α-chloroketone 2. The filtrate was concentrated to dryness and the residue was again recrystallized from $Et_2O$-hexane to give an additional 4.41 g (second crop) of α-chloroketone 2. Total yield: 13.99 g (92%).

(iv) Compound 3

3

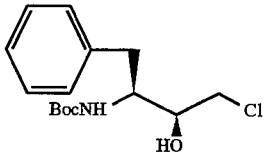

$NaBH_4$ (1.59 g; 42 mmol) was added to a solution of α-chloroketone 2 prepared above (5 g; 16.8 mmol) in 84 ml of THF and 9 ml of $H_2O$ at 0° C. After stirring at 0° C. for 45 min the reaction mixture was concentrated to dryness. The residue was stirred at 0° C. with EtOAc (150 ml) and $H_2O$ (25 ml) while saturated $KHSO_3$ solution was carefully added until the pH was ~1.5. This mixture was then diluted with 350 ml of EtOAc and the layers were separated. The organic layer was washed with $H_2O$ (100 ml) and brine (100 ml). After drying over $MgSO_4$, the organic layer was concentrated to a white solid. A portion of this solid (4.89 g) was recrystallized from 70 ml of hot EtOAc to afford 2.47 g (50%) of Compound 3 as a white solid containing a few percent of its diastereomer, the following Compound 4:

4

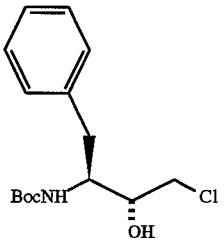

(v) Compound 5

5

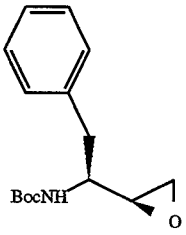

0.71M KOH in EtOH (14.7 ml; 10.4 mmol) was added to a suspension of Compound 3 (2.6 g; 8.67 mmol) in 87 ml of EtOH at RT. The reaction was stirred 1.5 h at RT, during which time the thick suspension became a fine powdery one. At this time, the EtOH was removed in vacuo and the residue was partitioned between EtOAc (200 ml) and $H_2O$ (200 ml). The organic layer was washed with saturated $NH_4Cl$ solution (2×100 ml), $H_2O$ (2×100 ml), and brine (100 ml). After drying over $MgSO_4$, the EtOAc was removed in vacuo and the solid white residue was recrystallized by dissolving in 10 ml of reluxing EtOAc and adding 190 ml of hexane. The resulting crystalline suspension was allowed to cool to −40° C. and stand overnight. Filtration, rinsing with hexane, and drying under high vacuum for two hours afforded 1.92 g (84%) of Compound 5 as a colorless crystalline solid. This material was 99.1% diastereomerically pure by HPLC.

(vi) Compound 6

6

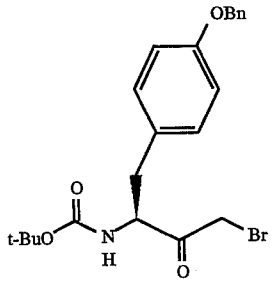

To a solution of N-Boc-0-benzyl-L-tyrosine (25.g, 67.3 mmol) in dry THF (90 ml) cooled at −20° C. was added isobutyl chloroformate (8.7 ml, 67.3 mmol) followed by 4-methylmorpholine (6.8 ml, 67.30 mmol) and the mixture was stirred for 20 minutes. The precipitate was filtered and washed with dry THF. The filtrate was cooled to −5° C. and poured into a diazomethane in ether solution (prepared from 1-methyl-3-nitro-1-nitrosoguanidine (29.7 g, 202 mmol) as described in (i) at 0° C. The resulting yellow solution was kept at 0° C. for 2.0 h, then at RT overnight. Nitrogen was then bubbled through the solution for 30 minutes, the solution diluted with $Et_2O$ (500 ml) and then washed with $H_2O$, sat'd $NaHCO_3$, and brine, and dried ($MgSO_4$). Concentration in vacuo afforded a yellow residue, which was triturated with hexane (500 ml) to give 24.5 g (92%) of the corresponding α-diazoketone as an off-white solid. A solution of 48% aqueous HBr (5.8 ml, 51.4 mol) was added dropwise to the α-diazoketone (20.3 g, 51.4 mmol) in 500 ml of 1,4-dioxane-DME (2:1) cooled at −5° C. After 30 minutes, saturated $NaHCO_3$ was added until pH=7.0 and the solvent was removed under reduced pressure. The mixture was diluted with $H_2O$ and extracted with EtOAc. The combined organic extracts were washed with $H_2O$ and brine and dried ($Na_2SO_4$). Concentration in vacuo followed by recrystallization from EtOAc-hexane gave 20.9 g (91%) Compound 6 as an off-white solid.

(vii) Compound 7

7

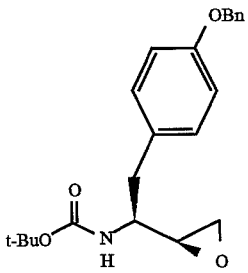

To a solution of Compound 6 (23.3 g, 50.0 mmol) in 250 ml of MeOH-THF (1:1) cooled at −5° C. was added, portionwise, $NaBH_4$ (2.0 g, 50.0 mmol). After 1 hour, 10% $KHSO_4$ (75 ml) was added at 0° C. and the mixture was allowed to warm to RT. The mixture was extracted with hot EtOAc and the combined organic extracts were washed with $H_2O$ and brine, and dried ($Na_2SO_4$). Concentration in vacuo followed by recrystallization from EtOAc (350 ml) afforded 14.5 g (62%) of the syn bromohydrin as a white solid. HPLC analysis showed the diastereomeric ratio as 95:5. To a solution of the syn bromohydrin, prepared as above (115.2 g, 0.256 mole), in 1.5 L of THF and 1.5 L of 100% EtOH was added a solution of KOH (17.2 g of 87.6% pellets, 0.269 mole) in 300 ml of 100% EtOH at RT. After 15 minutes, 1 liter of saturated aqueous $NH_4Cl$ was added and the mixture then diluted with 6 L of $H_2O$ to give a precipitate. The solid was filtered, washed with $H_2O$, and extracted into 1 liter of EtOAc. The organic phase was dried ($Na_2SO_4$) and concentrated in vacuo to give a solid which was triturated with 1 liter of hexane, to afford 79.3 g (84%) of Compound Z as a white solid.

(viii) Compound 8

8

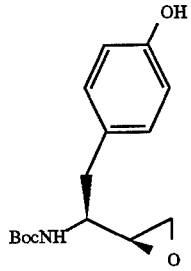

The mixture of Compound 7 (5.0 g, 13.5 mmol) and $Pd(OH)_2$ (500 mg) in 100 ml EtOH and 25 ml of EtOAc was stirred under hydrogen atmosphere for 4.5 hours. The catalyst was removed by filtration and the filter cake was washed with EtOH, MeOH, and EtOAc. The combined washes were concentrated in vacuo to give 3.8 g (99%) of Compound 8 as a white solid.

(ix) Compound 9

9

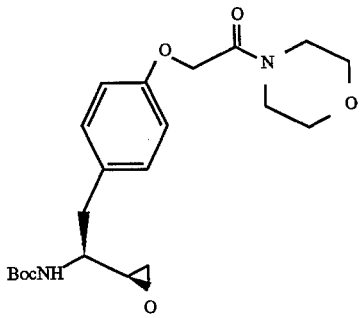

NaH (48 mg, 60% dispersion in mineral oil, 1.2 mmol) was washed twice with hexane and suspended in 1.0 ml of dry DMF. The suspension was cooled to 0° C. and a solution of Compound 8 (280 mg, 1.0 mmol) in 1.5 ml of dry DMF was added. The mixture was stirred at 0° C. for 30 minutes and then 4-(2-bromoacetyl)morpholine (J. Med. Chem., 35, 1685 (1992); 270 mg, 1.3 mmol) as added in one portion, followed by n-$Bu_4NI$ (185 mg, 0.5 mmol). The resulting mixture was stirred at RT overnight. After cooling to 10° C., $H_2O$ was added and the mixture extracted with EtOAc. The combined extracts were washed with $H_2O$ and brine, dried ($NaHCO_3$) and concentrated in vacuo to give a crude product which was purified by flash chromatography (hexane-EtOAc: 1:1 to 1:4) on silica gel to give 392 mg (96%) of Compound 9 as a white solid.

(x) Compound 10

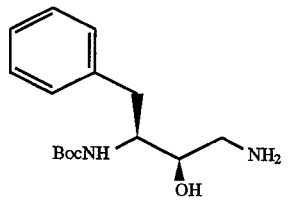

Compound 5 (15.0 g; 56.96 mmol) dissolved in 350 ml of EtOH was added, with stirring, over 1 h to 350 ml of concentrated $NH_4OH$ at 0° C. $NH_3$ gas was bubbled through the reaction mixture during the addition and for 1 hour after. The reaction was then warmed to RT and stirred overnight. The resulting slurry was diluted with 800 ml EtOAc and the organic layer washed repeatedly with brine. The organic extracts were dried ($MgSO_4$) and concentrated to give a white solid which was triturated with 10% i-PrOH/EtOAc to give 4.37 g of Compound 10. The mother liquors were evaporated and triturated again as above to give an additional 5.73 g of Compound 10 (total yield: 10.1 g; 63%).

(xi) Compound 11

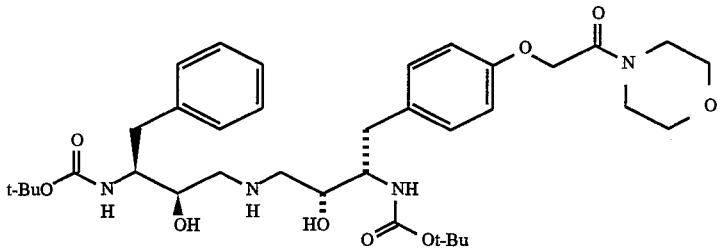

11

A mixture of Compounds 9 (407 mg, 1.0 mmol) and 10 (280 mg, 1.0 mmol) in 1.0 ml of dry DMF was heated at 100° C. for 4.0 h. Concentration in vacuo followed by flash chromatography ($CHCl_3$-MeOH-$NH_4OH$;98:2:0.2 to 95:5:0.5) on silica gel afforded 501 mg (73%) of Compound 11 as a white solid.

m.p. 118°–120° C.; $[\alpha]_D$=–4.7°, $[\alpha]_{365(Hg)}$=–23.6° (c 1.0, MeOH). Mass Spec. (FAB):687$^+$ $(M+H)^+$.

| Anal. Calc. for $C_{36}H_{54}N_4O_9.0.30H_2O$: | | | |
|---|---|---|---|
| | C, 62.46; | H, 7.95; | N, 8.09. |
| Found: | C, 62.46; | H, 7.91; | N, 8.28. |

What is claimed is:

1. A method for the prophylaxis or treatment of a disease caused by the HIV virus in a human patient, which comprises administering to said patient, either sequentially or concurrently, an effective HIV-inhibiting amount of an HIV-1 protease inhibitor compound of the formula

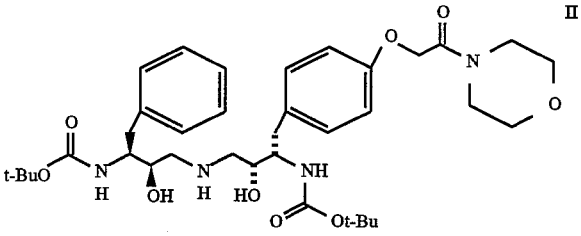

II or a pharmaceutically acceptable derivative thereof, and an effective HIV-inhibiting amount of one or more protease inhibitor compounds selected from the group consisting of (a) the compound of the formula

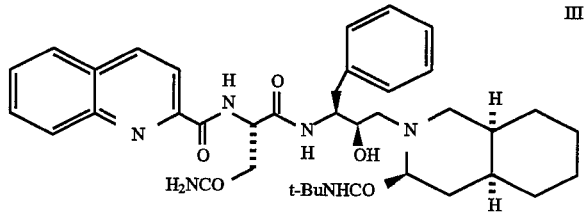

III or a pharmaceutically acceptable derivative thereof, (b) the compound of the formula

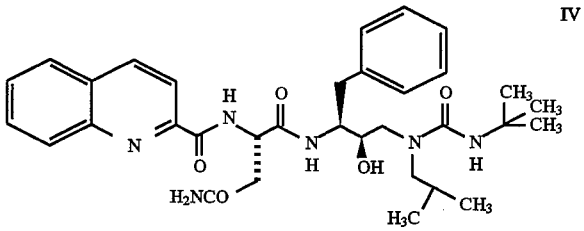

IV or a pharmaceutically acceptable derivative thereof, (c) the compound of the formula

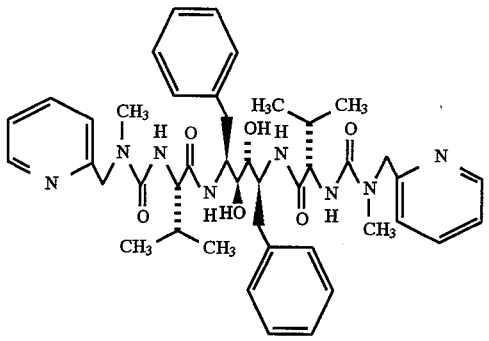

V or a pharmaceutically acceptable derivative thereof, (d) the compound of the formula

VI

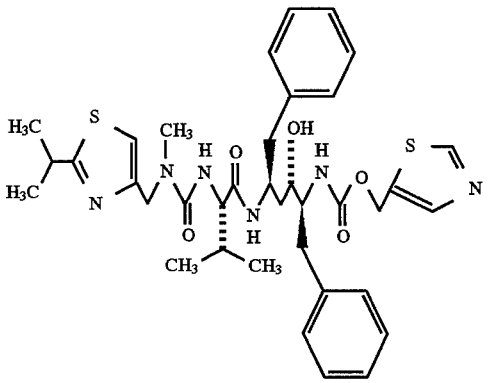

or a pharmaceutically acceptable derivative thereof, (e) the compound of the formula

VII

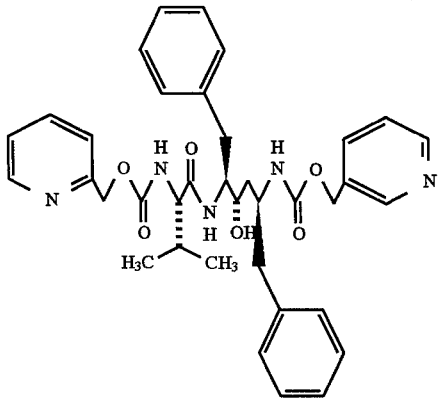

or a pharmaceutically acceptable derivative thereof, and (f) the compound of the formula

VIII

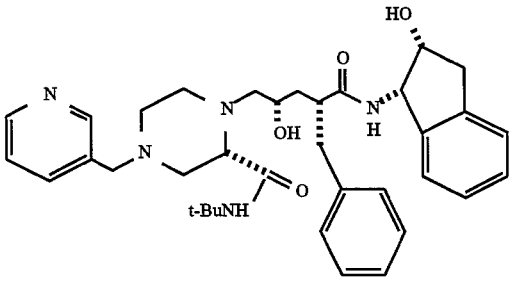

or a pharmaceutically acceptable derivative thereof, and (g) the compound of the formula

IX

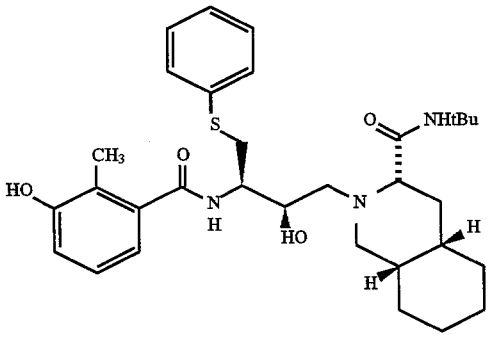

or a pharmaceutically acceptable derivative thereof.

2. The method according to claim 1 wherein there is employed the protease inhibitor of the formula

IX

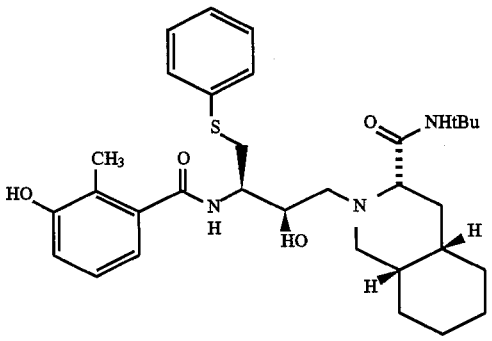

or a pharmaceutically acceptable derivative thereof.

3. A method of reducing or eliminating antiviral resistance resulting from administration to a human patient of a protease inhibitor selected from the group consisting of (a) the compound of the formula

III

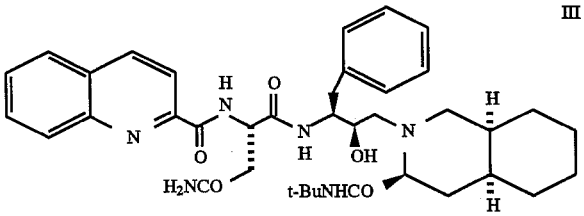

or a pharmaceutically acceptable derivative thereof, (b) the compound of the formula

IV

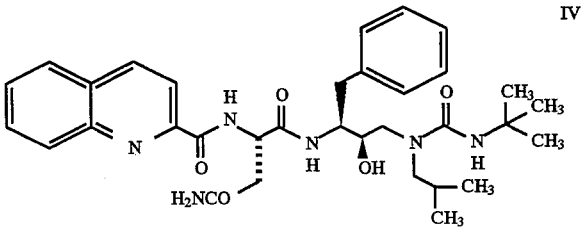

or a pharmaceutically acceptable derivative thereof, (c) the compound of the formula

V

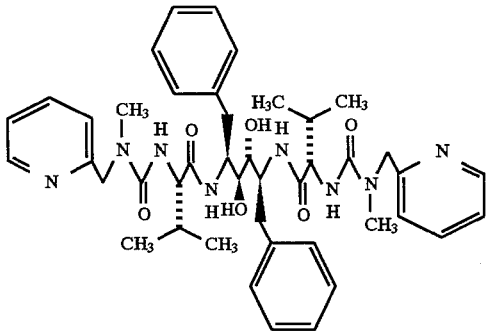

or a pharmaceutically acceptable derivative thereof, (d) the compound of the formula

VI

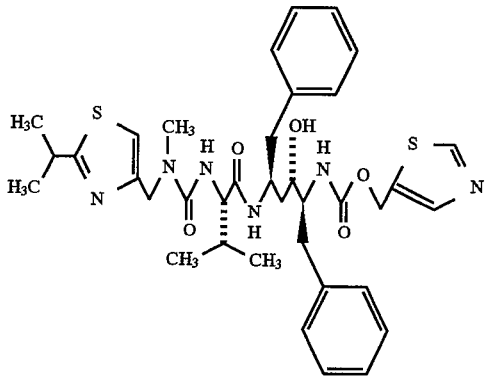

or a pharmaceutically acceptable derivative thereof, (e) the compound of the formula

VII

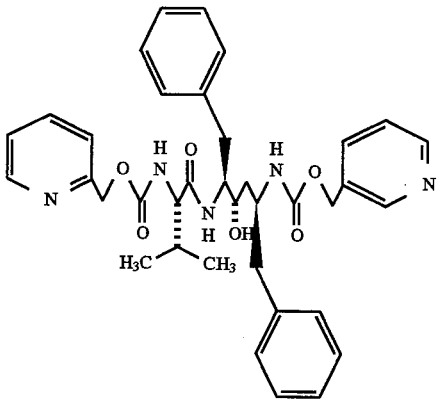

or a pharmaceutically acceptable derivative thereof, (f) the compound of the formula

VIII

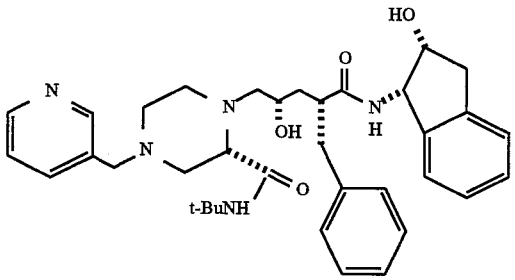

or a pharmaceutically acceptable derivative thereof and (g) the compound of formula

IX

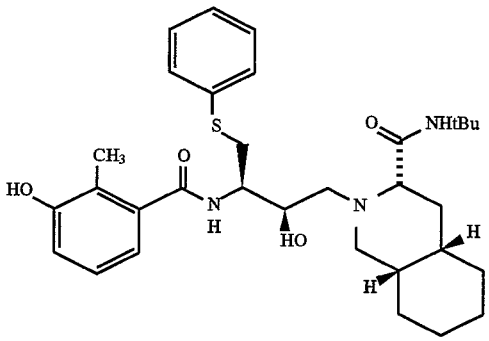

or a pharmaceutically acceptable derivative thereof, or a combination of two or more of said inhibitors, which comprises administering, either concurrently or sequentially, an effective HIV-inhibiting amount of a protease inhibitor having the formula

II

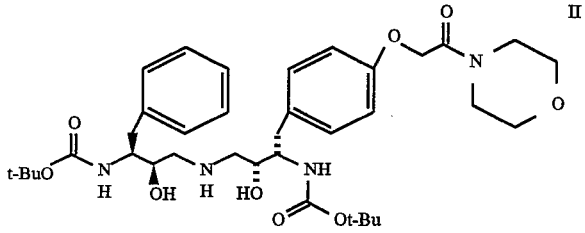

or a pharmaceutically acceptable derivative thereof.

4. The method according to claim 3 wherein the protease inhibitor of formula II, or a pharmaceutically acceptable derivative thereof, is administered in combination with a protease inhibitor of the formula

IX

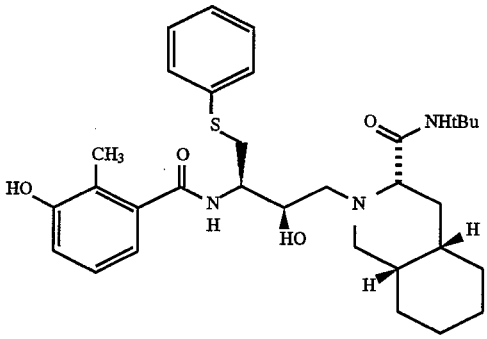

or a pharmaceutically acceptable derivative thereof.

5. A pharmaceutical composition for prophylaxis or treatment of a disease caused by the HIV virus comprising an effective HIV-inhibiting amount of a protease inhibitor compound of the formula

II

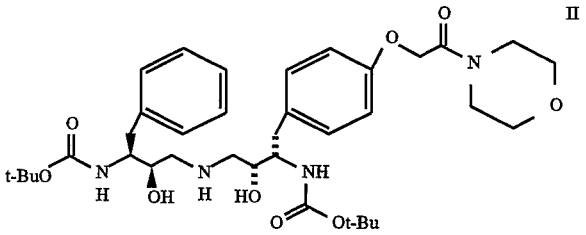

or a pharmaceutically acceptable derivative thereof and an effective HIV-inhibiting amount of one or more protease inhibitor compounds selected from the group consisting of (a) the compound of the formula

III

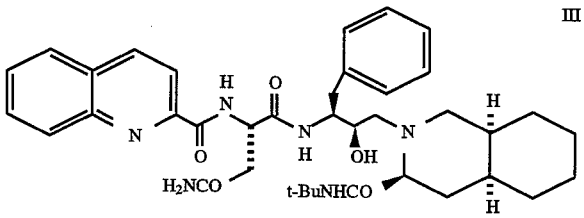

or a pharmaceutically acceptable derivative thereof, (b) the compound of the formula

IV

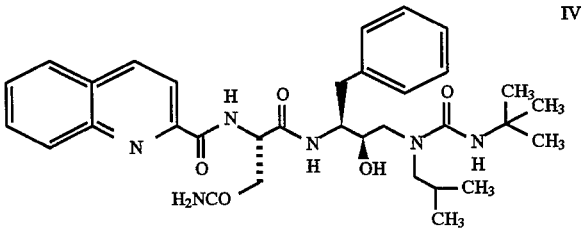

or a pharmaceutically acceptable derivative thereof, (c) the compound of the formula

V

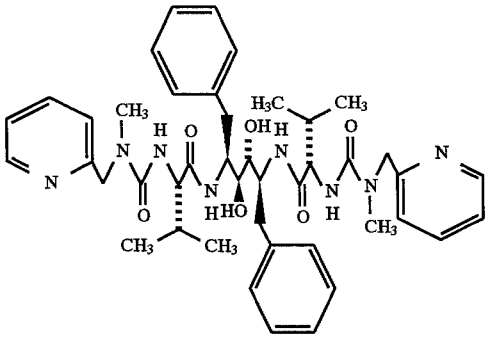

or a pharmaceutically acceptable derivative thereof, (d) the compound of the formula

VI

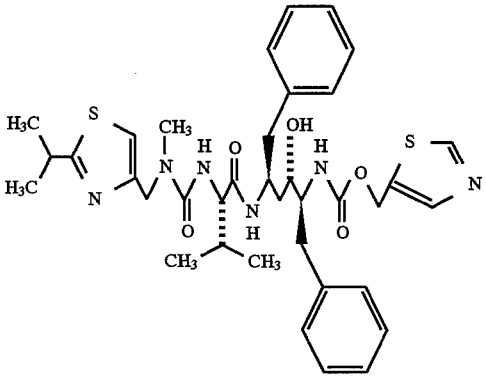

or a pharmaceutically acceptable derivative thereof, (e) the compound of the formula

VII

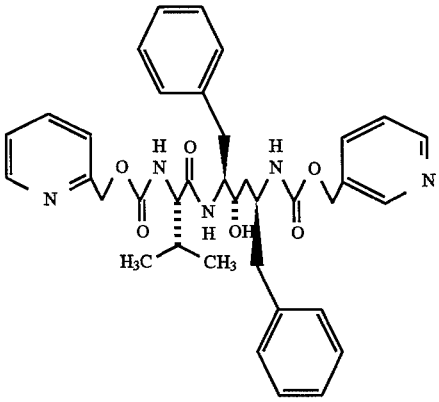

or a pharmaceutically acceptable derivative thereof, (f) the compound of the formula

VIII

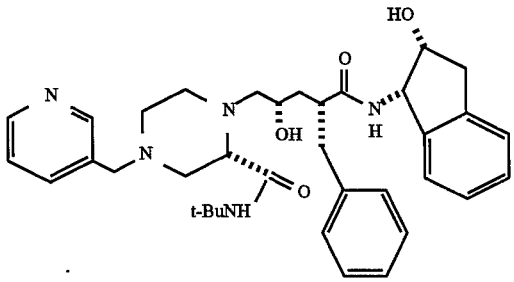

or a pharmaceutically acceptable derivative thereof, and (g) the compound of the formula

IX

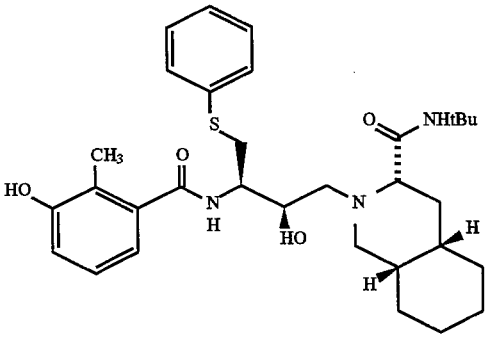

or a pharmaceutically acceptable derivative thereof in combination with a pharmaceutically acceptable carrier or diluent.

6. A composition according to claim 5 wherein the second protease is the compound of formula

IX

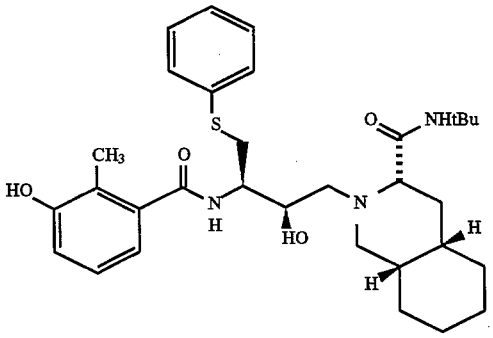

or a pharmaceutically acceptable derivative thereof.

* * * * *